United States Patent [19]

Markezich

[11] 4,020,089
[45] Apr. 26, 1977

[54] METHOD FOR MAKING N-ALKYLPHTHALIMIDES

[75] Inventor: Ronald L. Markezich, Scotia, N.Y.

[73] Assignee: General Electric Company, Schenectady, N.Y.

[22] Filed: July 1, 1975

[21] Appl. No.: 592,190

[52] U.S. Cl. .......................................... 260/326 R
[51] Int. Cl.² .................................... C07D 209/34
[58] Field of Search .............................. 260/326 R

[56] References Cited
UNITED STATES PATENTS 2,698,850  1/1955  Long et al. ..................... 260/326 R

FOREIGN PATENTS OR APPLICATIONS 2,056,891  5/1972  Germany ...................... 260/326 R Primary Examiner—Ethel G. Love
Attorney, Agent, or Firm—William A. Teoli; Joseph T. Cohen; Jerome C. Squillaro

[57] ABSTRACT

A continuous method is provided for making an N-alkylphthalimide, such as N-methylphthalimide, by effecting reaction between an alkylamine and phthalic anhydride at a temperature of at least 150° C, while providing for the removal of water of reaction. The N-alkylphthalimides are valuable precursors for making nitrophthalimide, organic dianhydrides and organic polymers.

1 Claim, 1 Drawing Figure

U.S. Patent     April 26, 1977     4,020,089
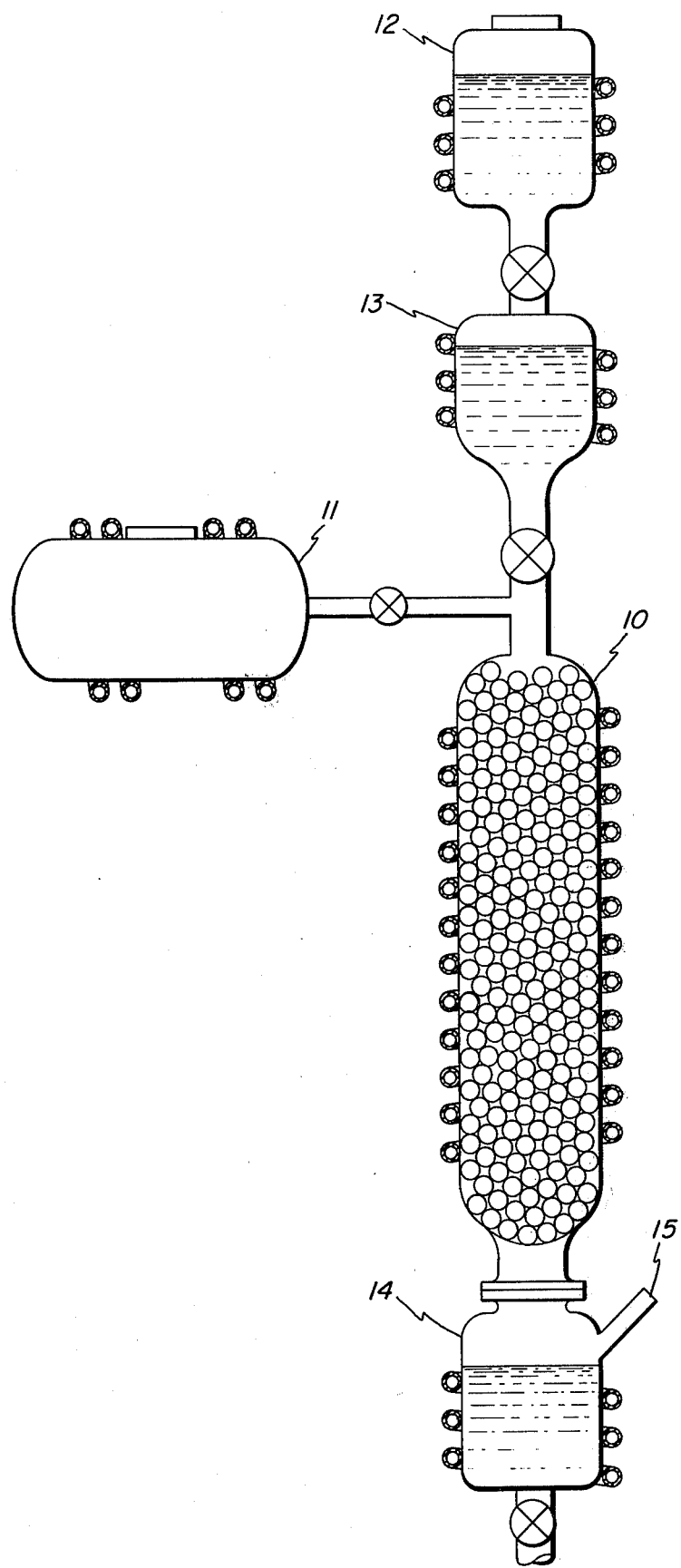

METHOD FOR MAKING N-ALKYLPHTHALIMIDES

The present invention relates to a method for making N-alkylphthalimide by using a hot tube reactor to effect reaction between an alkylamine and phthalic anhydride.

Improved methods for making N-alkylphthalimides are constantly being sought as these intermediates can be converted to nitro N-alkylphthalimides which are basic starting reactants for making a variety of organic dianhydrides and polyimides as shown by Heath et al. U.S. Pat. No. 3,879,428 assigned to the same assignee as the present invention. Prior to the resent invention, one method for making N-alkylphthalimides involved the treatment of phthalic anhydride with aqueous alkylamine followed by distillation of the product. For obvious reasons, this procedure is unsatisfactory for continuous production of N-alkylphthalimides in an economic manner, since water is a diluent and it must be eliminated along with water of reaction. Another method involves the treatment of phthalic anhydride in acetic acid with an alkylamine.

Experience has shown that attempts to make N-alkylphthalimides from phthalic anhydride and N-alkylamines under melt conditions often results in the production of the corresponding bis(n-alkyl)amide. The nitration of N-alkylphthalimide containing significant amounts of bis-(N-alkyl)amide of phthalic acid can result in nitration products unsuitable for the production of organic dianhydrides and polyimides.

Although many of the methods of the prior art were satisfactory for making N-alkylphthalimides in a batchwise manner, large scale production of N-alkylphthalimides in an economic manner requires a continuous method.

The present invention is based on the discovery that a hot tube reactor can be used to produce N-alkylphthalimides in a continuous manner by directly contacting N-alkylamine and phthalic anhydride. Surprisingly, the yield of the N-alkylphthalimides are quantitative and reaction can be achieved in less than a minute. The N-alkylphthalimide is produced substantially free of the corresponding bis(N-alkyl)amide of phthalic anhydride.

There is provided by the present invention a method for making N-alkylphthalimides which comprises,
1. introducing a gaseous mixture consisting essentially of an alkylamine into a reaction zone,
2. gravitating fluid phthalic anhydride into the reaction zone of (1) at a temperature of from about 150° C to 500° C,
3. allowing sufficient time to effect reaction between the phthalic anhydride fluid and the gaseous mixture consisting essentially of alkylamine,
4. venting water of reaction from the reaction zone while collecting N-alkylphthalimide as it forms therefrom.

The drawing is a side view of an apparatus having a fluid phthalic anhydride source, a source of gaseous alkylamine, a hot tube reactor and a means for venting water of reaction, and a means for collecting N-alkylphthalimide.

More particularly at 10, there is shown a reactor surrounded by a heating means and filled with a static bed, such as glass beads, stainless steel beads, procelain beads or chips, steel wool, ceramic beads, etc.

A tank of alkylamine is shown at 11, which also has a heating coil if heat is required. Phthalic anhydride vessels having heating coils and control valves are shown at 12 and 13 to allow for charging crystalline phthalic anhydride at 12, heating it to the fluid state and controlling its flow into the reactor. A control valve is also shown for the tank at 11, to control the flow of alkylamine into the reactor.

A vessel for collecting liquid N-alkylphthalimide substantially free of bis(N-alkyl)amide of phthalic anhydride is shown at 14 with a vent for water of reaction at 15, a heat means to maintain the N-alkylphthalimide in the liquid state and a flow control valve for collecting the liquid N-alkylphthalimide.

In the practice of the invention, phthalic anhydride is charged to the heating vessel as shown in the drawing. The jacketed hot tube is maintained at a temperature of about 300° C. Liquid phthalic anhydride is allowed to flow into the hot tube reactor fluid while alkylamine is introduced into the side as shown. Depending upon such factors as the capacity of the hot tube, which can vary in length from between about 0.5 feet to 50 feet, the flow rate of the phthalic anhydride to the tube can vary from about 0.1 part per minute to 100 parts per minute. Preferably, the alkylamine is introduced into the reactor at a flow rate of 0.01 parts to 10 parts per minute. Prior to the introduction of the phthalic anhydride it has been found that if an inert gas is used with the alkylamine, such as nitrogen, helium, etc., the venting of water of reaction can be facilitated. Reaction time can be effected in as little as 0.01 minute or less or 10 minutes or more, depending upon such factors as the capacity of the reactor, temperature, etc.

In order that those skilled in the art will be better able to practice the invention, the following examples are given by way of illustration and not by way of limitation. All parts are by weight.

EXAMPLE 1

An addition funnel is charged with 46 parts of phthalic anhydride. After the anhydride is melted, it is added as a slow stream through an adaptor heated at 250° C containing a side arm. The adaptor is connected to a glass tube filled with glass beads. Through the side arm of the adaptor there is introduced methylamine gas. The mixture of the methylamine gas and the liquid phthalic anhydride is allowed to flow into the glass tube heated at 300° C which contains glass beads. At the bottom of the glass tube there is a receiver in the form of 100 ml flask fitted with a side arm. The methylamine gas is introduced at a rate of 1–2 parts per minute. The addition of the molten phthalic anhydride is completed in about 10–15 minutes while excess methylamine and water produced in the reaction being vented through the side arm. There is obtained a 72% yield of N-methylphthalimide as a white solid having a melting point of 129.5°–132° C. No unreacted phthalic anhydride and less than 1% by weight of bis-(N-methyl)amide of phthalic anhydride was detected in the final product based on liquid chromotography.

EXAMPLE 2

An addition funnel is charged with 50 parts of phthalic anhydride. After the anhydride is melted, it is added as a slow stream through an adaptor heated at 250° C containing a side arm. The adaptor is connected to a glass tube filled with glass beads as in Example 1. Through the side arm of the adaptor there is introduced an excess of ethylamine gas. The mixture of the ethylamine gas and the liquid phthalic anhydride is allowed to flow into a glass tube containing glass beads and heated to 300° C. The ethylamine is introduced at a rate of 1.0–1.5 parts per minute. The addition of the molten phthalic anhydride is completed in about 10–15 minutes while excess ethylamine and water produced in the reaction being vented through the side arm. N-ethylphthalimide containing less than 1% by weight of bis(N-ethyl)amide of phthalic anhydride is collected in the receiver as a white solid, mp 79°.

EXAMPLE 3

As shown in the drawing, fluid phthalic anhydride and methylamine are continuously introduced into a reactor at a temperature of 250° C. A slight excess of methylamine is maintained in the reactor at all times. When the receiver is full, N-methylphthalimide is removed as a liquid. Water is continuously vented out. Crystalline phthalic anhydride is charged to the vessel at top and converted to the molten state before it is allowed to collect as a fluid in the containing vessel prior to its introduction into the reactor.

Although the above examples are limited to only a few of the variables which can be involved in the practice of the invention, it should be understood that the method of the invention involves the use of a broader class of alkylamines such as propylamine, butylamine, etc.

What I claim as new and desire to secure by Letters Patent of the United States is:

1. A continuous method for making N-methylphthalimide which comprises,
   1. introducing a gaseous mixture consisting essentially of methylamine and an inert gas into a reaction zone,
   2. gravitating fluid phthalic anhydride into the reaction zone of (1) at a temperature of from about 150° C to 500° C,
   3. allowing sufficient time to effect reaction between the phthalic anhydride fluid and the gaseous methylamine
   4. venting water of reaction from the reaction zone while collecting N-methylphthalimide as it forms therefrom, where the gaseous mixture of step 1 is maintained at a rate which is sufficient to provide at least a slight excess of methylamine in the reactor at all times.

* * * * *